(12) United States Patent
Cha

(10) Patent No.: US 8,431,083 B2
(45) Date of Patent: *Apr. 30, 2013

(54) MICROWAVE INDUCED DESTRUCTION OF SILOXANES AND HYDROGEN SULFIDE IN BIOGAS

(75) Inventor: Chang Yul Cha, Roseville, CA (US)

(73) Assignees: Cha Corporation, McClellan, CA (US); C-Micro Systems, Inc., Vaudreuil-Dorion, QC (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/365,939

(22) Filed: Feb. 3, 2012

(65) Prior Publication Data

US 2012/0301366 A1    Nov. 29, 2012

Related U.S. Application Data

(60) Continuation of application No. 13/099,586, filed on May 3, 2011, now Pat. No. 8,168,126, which is a division of application No. 12/013,922, filed on Jan. 14, 2008, now Pat. No. 7,960,303.

(60) Provisional application No. 60/884,983, filed on Jan. 15, 2007.

(51) Int. Cl.
  *B01D 50/00*    (2006.01)
(52) U.S. Cl.
  USPC .......................................... 422/178; 422/619
(58) Field of Classification Search ............... 502/34, 502/56; 422/144, 178, 619; 423/210
See application file for complete search history.

(56) References Cited

U.S. PATENT DOCUMENTS

| 3,760,242 A | 9/1973 | Duffy et al. |
| 3,853,567 A | 12/1974 | Verbeek |
| 5,152,970 A | 10/1992 | van der Wal et al. |
| 5,246,554 A | 9/1993 | Cha |
| 5,256,265 A | 10/1993 | Cha |
| 5,269,892 A | 12/1993 | Cha |
| 5,362,451 A | 11/1994 | Cha |
| 5,508,208 A | 4/1996 | Sato |
| 5,536,477 A | 7/1996 | Cha et al. |
| 5,589,599 A | 12/1996 | McMullen et al. |
| 5,767,470 A | 6/1998 | Cha |

(Continued)

OTHER PUBLICATIONS

Liang, K.Y. et al.—"Removing Siloxanes: Solution to Combustion Equipment Problems"—WEFTEC, Oct. 2002, pp. 1-11.

(Continued)

*Primary Examiner* — Edward Johnson
(74) *Attorney, Agent, or Firm* — John P. O'Banion

(57) ABSTRACT

The invention is an apparatus and method to remove hydrogen sulfide and siloxanes from biogas and destroy the contaminants in microwave reactors. Hydrogen sulfide and siloxane are removed from biogas using an adsorbent media such as activated carbon. The media is regenerated in a microwave reactor where the hydrogen sulfide and siloxane are removed in a sweep gas. In one process, siloxane is oxidized to silicon dioxide in a second microwave reactor and removed with a filter. Hydrogen sulfide if first oxidized to sulfur dioxide, then reduced to sulfur in a third microwave reactor and removed with a filter. In another process, siloxane is combined with water to form silicon dioxide and hydrogen sulfide is reduced to elemental sulfur in a microwave reactor. These reactants are removed with a filter. The remaining sweep gas containing hydrogen and low molecular weight hydrocarbons is returned to the biogas stream.

9 Claims, 5 Drawing Sheets

U.S. PATENT DOCUMENTS

| | | | |
|---|---|---|---|
| 5,843,236 | A | 12/1998 | Yoshiki et al. |
| 5,904,750 | A | 5/1999 | Cowles |
| 6,027,698 | A | 2/2000 | Cha |
| 6,207,023 | B1 | 3/2001 | Cha |
| 6,284,202 | B1 | 9/2001 | Cha et al. |
| 6,419,799 | B1 | 7/2002 | Cha |
| 6,592,723 | B2 | 7/2003 | Cha |
| 6,783,632 | B2 | 8/2004 | Cha |
| 6,830,662 | B2 | 12/2004 | Cha |
| 7,641,874 | B2 | 1/2010 | Cha |
| 7,960,303 | B2 | 6/2011 | Cha |
| 8,168,126 | B2 * | 5/2012 | Cha .............................. 422/178 |
| 2003/0038251 | A1 | 2/2003 | Livesay et al. |
| 2006/0000352 | A1 | 1/2006 | Tower et al. |
| 2007/0126649 | A1 | 6/2007 | Cha et al. |
| 2010/0143209 | A1 | 6/2010 | Cha |

OTHER PUBLICATIONS

Williams, R.B.—"Biofuels from Municipal Wastes-Background Discussion Paper"—The California Biomass Forum, Mar. 28, 2007, pp. 1-28.

Tower, P.—"New Technology for Removal of Siloxanes in Digester Gas Results in Lower Maintenance Costs and Air Quality Benefits in Power Generation Equipment"—WEFTEC 03, 78th Annual Technical Exhibition and Conference, Oct. 11-15, 2003, pp. 1-9.

AFT online SWOP brochure—"Complete Contaminant Removal"—2007, downloaded from the internet from www.appliedfiltertechnology.com, 1 page.

Tower, P. et al.—"New Landfill Gas Treatment Technology Dramatically Lowers Energy Production Costs"—Annual SWANA Landfill Gas Symposium, 2006, pp. 1-15.

Tower, P.—"Siloxanes and Other Harmful Contaminants: Their Importance in Total LFG Quality Management"—SWANA 27th Landfill Gas Symposium, Mar. 24, 2004, pp. 1-9.

Tower, P.—"Removal of Siloxanes From Land Gas by SAG Polymorphous Porous Graphite Treatment Systems"—SWANA 26th Landfill Gas Symposium, Mar. 27, 2003, pp. 1-10.

Tower, P. et al.—"Reducing Biogas Power Generation Costs by Removal of Siloxanes"—SWANA 26th Landfill Gas Symposium, Mar. 27, 2003, pp. 1-20.

Tower, P. et al.—"Making Power Generation Make Sense by Removing Siloxanes from Digester Gas"—California Water Environment Association Conference, Apr. 2006, pp. 1-5.

AFT SAGPack online brochure—"SAGPack Biogas Treatment Process"—2007, downloaded from the internet from www.appliedfiltertechnology.com, 1 page.

Slowe, J. et al.—"Biogas: A Growing Niche for Distributed Generation"—E Source, DE-21, May 2003, pp. 1-31.

Wheless, E. et al.—"Siloxanes in Landfill and Digester Gas Update"—SWANA, 2004, pp. 1-9.

Nourot, M.—"Operational Costs and Other Considerations of Landfill Gas Cleaning"—2006 LMOP Conference, pp. 1-20.

Zicari, S.—"Removal of Hydrogen Sulfide From Biogas Using Cow-Manure Compost"—Thesis at Cornell University, Jan. 2003, 132 pages.

Cha, C.—"Microwave Technology for Superfund Site Remediation"—NIEHS Project Bried, Jul. 2003, pp. 1-4.

United States Patent & Trademark Office (USPTO)—International Search Report and Written Opinion issued on May 20, 2008, including claims searched, related PCT International Application No. PCT/US08/51008, pp. 1-17.

USPTO, Final Office Action Issued on Jul. 18, 2012 (pp. 1-16), including claims examined (pp. 17-19), U.S. Appl. No. 12/621,259, pp. 1-19.

* cited by examiner

MICROWAVE INDUCED DESTRUCTION OF SILOXANES AND HYDROGEN SULFIDE IN BIOGAS

CROSS-REFERENCE TO RELATED APPLICATIONS

This application is a continuation of U.S. patent application Ser. No. 13/099,586 filed on May 3, 2011, incorporated herein by reference in its entirety, which is a division of U.S. patent application Ser. No. 12/013,922 filed on Jan. 14, 2008, now U.S. Pat. No. 7,960,303, incorporated herein by reference in its entirety, which is a nonprovisional of U.S. provisional application Ser. No. 60/884,983 filed on Jan. 15, 2007, incorporated herein by reference in its entirety. Priority is claimed to each of the foregoing applications.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to destruction of contaminants in biogas, and more particularly to microwave induced destruction of siloxanes and hydrogen sulfide contaminants from biogas.

2. Description of Related Art

Developing biogas resources for electric generation is challenging because of pretreatment requirements to accommodate the generating equipment and combustion controls or post treatment systems needed to meet increasingly stringent emission requirements, especially in California. Removing siloxanes and hydrogen sulfide ($H_2S$) from biogas is crucial because their combustion products increase engine maintenance intervals and interfere with existing post-combustion nitrogen oxides (NOx), sulfur oxides (SOx), and hydrocarbon removal technologies that are required to meet regional air quality standards.

Siloxanes are a family of man-made organic compounds that contain silicone, oxygen and methyl groups. As a consequence of their widespread use in consumer products, siloxanes are found in wastewater and in solid waste deposited in landfills. At wastewater treatment plants and landfills, low molecular weight siloxanes volatilize into digester and landfill gas. When this biogas is combusted in gas turbines, boilers, or internal combustion engines, siloxanes are converted to silicon dioxide ($SiO_2$) and micro-crystalline quartz, which can deposit in the combustion and/or exhaust stages of the equipment as an abrasive white powder, contributing to engine wear and component failure. Landfills have siloxane concentrations on average from as low as 0.2 mg/m$^3$ to about 10 mg/m$^3$ but can be as high as about 140 mg/m$^3$. Siloxane concentrations can vary greatly in landfills as they age whereas the concentration in wastewater digesters is fairly constant. Animal waste digesters typically contain little or no siloxane unless offsite waste material is added. Manufacturers of combustion turbines and reciprocating engines have begun limiting feed gas siloxane concentrations to between 5-28 mg/m$^3$ for internal combustion (IC) engines, and 0.1 to 0.03 mg/m$^3$ for gas turbines.

Table 1 presents common volatile siloxanes found in biogas with their molecular weight, vapor pressure, boiling point, chemical formula, and water solubility. Abbreviations are commonly used to identify the siloxane compounds. Siloxanes that are cyclic in structure have a single abbreviation of D. Siloxanes that have a linear structure have two abbreviations using an L or M nomenclature.

Additional organosilicon compounds such as Trimethylsilanol ($Si(CH_3)_3OH$) and Tetramethylsilane ($Si(CH_3)_4$) may also be present in biogas and are included in the term siloxane for purposes of describing this invention.

Both wet and dry scrubbers have been used to remove siloxanes from biogas. The major disadvantages of wet scrubbers are the production of hazardous liquid waste and the fact that complete silicon elimination is difficult to obtain since the highly volatile siloxanes are stripped from the solvent at elevated gas flow rates.

Cyclic and linear (dimethyl) siloxanes are very stable against chemical and biochemical degradation. However, strong acids or bases catalyze the cleavage of Si—O bonds to produce poly dimethyl siloxanes. Due to the high content of $CO_2$ in biogases, the application of caustic absorbents for siloxane removal is not practical due to carbonate formation. Using acidic solutions is also difficult due to the hazardous liquid wastes.

The most common adsorbent used in dry scrubbing is Granular Activated Carbon (GAC), because it is cheaper than alternative adsorbents such as molecular sieves and polymer beads. GAC adsorbs siloxanes, $H_2S$, heavy hydrocarbons and organic halides. Since siloxanes are difficult to desorb from GAC, the adsorbent must be replaced regularly. The siloxane saturated GAC is typically burned as fuel or disposed of in a landfill where the volatile compounds, including siloxanes, can reappear is subsequent landfill gas. Other contaminants, such as $H_2S$, compete with siloxanes for adsorption sites on the GAC. Temperature and water content of the biogas also affects GAC adsorption capacity. Different siloxane compounds will also exhibit different adsorption capacities, generally with adsorption capacity increasing with increasing molecular weight.

Chilling biogas down to 40 deg F. is used to dry the gas for turbines and also removes siloxane in a range of 15% to about 50%. A proprietary process that refrigerates biogas to about −20 deg F. claims 95-99% siloxane removal rates. Both refrigeration processes use a GAC adsorber for final siloxane removal. Refrigeration uses significant energy to clean the biogas.

Consequently, GAC is currently the most practical and economic adsorbent for the removal of siloxanes in biogas. A better reactivation technology to desorb high molecular weight siloxanes can remove the need to chill the biogas and reduce the major lifecycle cost of GAC systems, which is carbon replacement. As discussed later, microwave energy can easily remove high molecular weight siloxanes from GAC.

Anaerobic digesters produce about 50%-60% methane, 40%-50% $CO_2$ and sulfur impurities mostly in the form of $H_2S$. Landfill gas typically has lower methane concentrations and added hydrocarbons derived primarily from solvents in the landfill. Landfill gas and digester gas may also contain a variety of trace compounds. More than 140 substances have been identified so far and they reach a total concentration of up to 2000 mg/m$^3$ (0.15% by volume). During the combustion process, $H_2S$ and halogenated compounds in biogas form corrosive acids including $H_2SO_4$ and HCl.

Hydrogen Sulfide has a strong odor that can be detected at threshold levels of about 0.47 parts per billion (ppb) and has an OSHA IDLH level of 300 parts per million (ppm). Digesters have $H_2S$ levels of about 25 ppm to over 1,000 ppm for animal digesters, where landfills gas levels usually vary from 10 ppm to over 100 ppm. Assuming emissions of SOx are not an issue, boilers can tolerate $H_2S$, levels up to 1,000 ppm, reciprocating engines about 10 to 100 ppm and fuel cells 10 ppm to 20 ppm.

Reciprocating engines operating on digester biogas compared to natural gas engines cost about 20% more to install and about 80% more to maintain. Sulfur plugs filters, causes deposits on valves and cylinders and contaminates lubricating oil. It has been reported that some operators must change spark plugs frequently ($1,000 annually) and change oil as often as weekly ($350 to $1,000 per month).

The $H_2S$ pretreatment system of choice for digesters with 100 to 1,000+ ppm $H_2S$ has been gas contact with an iron oxide media. The most well known treatment system is an iron sponge. This is a container of iron oxide impregnated media (typically woodchips) that scrubs the inlet gas from the digester. The iron sponge is sized for a residence time of about 60 seconds and, the media can collect up to about 2.5 times its weight in sulfur compounds. The media can be partially regenerated by exposure to air or by wetting for about 10 days. Eventually the media must be discarded and replaced with new media. With increasing frequency, the spent media is classified a hazardous waste by local regulators. One example of an iron sponge system costs about $50,000 to install with annual operating costs ranging from $250 to $4,000.

Proprietary iron-oxide media such as SulfaTreat®, Sulfur-Rite®, and Media-G2® have been installed as improved alternatives to the iron sponge at a few digester sites. These use different media and additional chemical treatment to remove sulfur. Some of these media have limited regeneration capacity or can be safely deposited in a landfill. One dairy digester site using Media-G2 has two vessels with about 760 kg of media each with a residence time of about 62 seconds per vessel. Annual media consumption ranges from 1,460 kg to about 5,900 kg with media replacement costs on the order of $2,050 to $8,290.

GAC and other carbon products are used extensively for filtration of contaminants in water and gas streams. GAC contains micro-pores that capture and hold many organic and polar molecules and is more effective for larger molecules. In other cases, the carbon acts as a catalyst to drive a reaction with the carbon and the selected molecule in a process known as chemisorption.

Commercially available GAC and Pelletized Activation Carbon (PAC) have the surface area in the range of 800-1000 m$^2$/g. These activated carbons easily adsorb $SO_2$, NOx, and VOCs. The carbon adsorption capacity is dependent on the composition of gas. GAC and PAC also adsorb siloxanes and $H_2S$ in biogas.

GAC adsorbs most VOCs and is used in removing common solvent vapors used in drying cleaning and parts washing operations. The carbon adsorption capacity is strongly dependent on the VOC molecular weight. The adsorption capacities of toluene and methylene chloride at the room temperature are 20 and 5 g/100 g GAC, respectively. However the adsorption capacity of $CH_4$ in GAC is negligible.

The GAC adsorption capacity for $H_2S$ is 5-15% by weight depending on loading of water and other contaminants. Therefore, GAC can be used economically to remove the $H_2S$ from biogas that contains lower concentrations of $H_2S$. Typically, used GAC is disposed of in a landfill when saturated with $H_2S$.

Impregnating GAC with alkaline or oxide solids enhance the physical adsorptive characteristics of the carbon with chemical reaction. Sodium hydroxide (NaOH), sodium carbonate ($Na_2CO_3$), and potassium hydroxide (KOH) are common impregnators. The metal oxide impregnation increases the GAC adsorption capacity significantly-especially if a small amount of oxygen is present in the biogas stream. Typically, 20-25% loading by weight of $H_2S$ can be achieved. The metal-impregnated GAC is almost twice more expensive than GAC. However, the use of metal-impregnated GAC will be more economical for the adsorbers without the on-site carbon reactivation because of its greater adsorption capacity. If the on-site GAC regeneration is available, the use of regular GAC for $H_2S$ removal is preferable to the metal oxide-impregnated GAC.

The GAC adsorption capacity for Siloxanes has been reported to be from 1 to 1.5 percent by weight. This capacity is affected by the species of Siloxane in the gas, other contaminants in the gas including $H_2S$, and the temperature and water content of the gas.

Once GAC can no longer adsorb a chemical compound, breakthrough will occur where the compound will flow all the way through the bed without being adsorbed. At this point, the GAC is no longer effective and must be replaced. In many cases, such as GAC filled water filters or respirators, the GAC is thrown away and a fresh GAC filter or cartridge is installed. In large scale processes, or where the contaminant can be recovered or destroyed, regeneration of the GAC may be preferred.

There are four processes commonly used for GAC regeneration: Temperature Swing Adsorption (TSA), Pressure Swing Adsorption (PSA) Inert Purge and Displacement Purge. TSA takes place by heating the GAC to remove contaminants. With PSA the adsorption takes place at an elevated pressure and regeneration at a lower pressure. Inert gas purge reduces the partial pressure of the adsorbate in the gas phase so that desorption occurs. A purge gas that is more strongly adsorbed than the contaminant is used to desorb the original contaminant. Steam regeneration is a combination of TSA and purge. In each process, the contaminant is still present in the purge stream and must be captured, burned or vented to the atmosphere.

High molecular weight siloxane compounds make conventional thermal regeneration difficult due to their low vapor pressures. Heavy molecules accumulate in GAC after thermal regeneration, limiting the number of activation cycles carbon can by subject to before its performance is inadequate.

A molecular sieve is a material containing tiny pores of a precise and uniform size that is used as an absorbent for gases and liquids. Molecules small enough to pass through the pores are absorbed while larger molecules are not. It is different from a common filter in that it operates on a molecular level. For instance, a water molecule may be small enough to pass through while larger molecules are not. Because of this, they often function as a desiccant. A molecular sieve can absorb water up to 22% of its own weight so removal of water in biogas is important. Often they consist of aluminosilicate minerals, clays, porous glasses, microporous charcoals, zeolites, active carbons, silica gel or synthetic compounds that have open structures through which small molecules, such as nitrogen and water can diffuse. They are classified by pore size such as type 3A or type 4A designating pore size in angstroms. Traditional methods for regeneration of molecular sieves include pressure change, as in oxygen concentrators, or by heating and purging with a carrier gas. Molecular sieve materials can also be regenerated in a microwave system.

Quantum radiofrequency (RF) physics is based upon the phenomenon of resonant interaction with matter of electromagnetic radiation in the microwave and RF regions since every atom or molecule can absorb, and thus radiate, electromagnetic waves of various wavelengths. The rotational and vibrational frequencies of the electrons represent the most important frequency range. The electromagnetic frequency spectrum is usually divided into ultrasonic, microwave, and optical regions. The microwave region is from 300 megahertz (MHz) to 300 gigahertz (GHz) and encompasses frequencies used for much communication equipment. For instance, refer to Cook, Microwave Principles and Systems, Prentice-Hall, 1986.

Often the term microwaves or microwave energy is applied to a broad range of radiofrequency energies particularly with respect to the common heating frequencies, 915 MHz and 2450 MHz. The former is often employed in industrial heating applications while the latter is the frequency of the common household microwave oven and therefore represents a good frequency to excite water molecules. In this writing the term "microwave" or "microwaves" is generally employed to represent "radiofrequency energies selected from the range of about 500 to 5000 MHz", since in a practical sense this large range is employable for the subject invention.

The absorption of microwaves by the energy bands, particularly the vibrational energy levels, of atoms or molecules results in the thermal activation of the nonplasma material and the excitation of valence electrons. The nonplasma nature of these interactions is important for a separate and distinct form of heating employs plasma formed by arc conditions at a high temperature, often more than 3000 .degree. F., and at much reduced pressures or vacuum conditions. For instance, refer to Kirk-Othmer, Encyclopedia of Chemical Technology, 3rd Edition, Supplementary Volume, pages 599-608, Plasma Technology. In microwave technology, as applied in the subject invention, neither of these conditions is present and therefore no plasmas are formed.

Microwaves lower the effective activation energy required for desirable chemical reactions since they can act locally on a microscopic scale by exciting electrons of a group of specific atoms in contrast to normal global heating which raises the bulk temperature. Further this microscopic interaction is favored by polar molecules whose electrons become easily locally excited leading to high chemical activity; however, nonpolar molecules adjacent to such polar molecules are also affected but at a reduced extent. An example is the heating of polar water molecules in a common household microwave oven where the container is of nonpolar material, that is, microwave-passing, and stays relatively cool.

In this sense microwaves are often referred to as a form of catalysis when applied to chemical reaction rates; thus, in this writing the term "microwave catalysis" refers to "the absorption of microwave energy by carbonaceous materials when a simultaneous chemical reaction is occurring" For instance, refer to Kirk-Othmer, Encyclopedia of Chemical Technology, 3rd Edition, Volume 15, pages 494-517, Microwave Technology.

BRIEF SUMMARY OF THE INVENTION

The features of the present invention include (1) removal of silxoanes, $H_2S$ and hydrocarbons from biogas with adsorbent media, (2) microwave reactivation of adsorbent media containing siloxanes and $H_2S$, (3) microwave-induced oxidation of siloxanes and $H_2S$ in the SiC catalyst bed, and (4) microwave-induced reduction reaction of $SO_2$ with GAC to produce elemental sulfur and carbon dioxide. The media adsorber concentrates siloxanes and $H_2S$ from biofuel gas into the media, which leads to a small, concentrated contaminant stream during microwave regeneration.

High molecular weight siloxane compounds make conventional thermal regeneration difficult due to their low vapor pressures. Since microwaves penetrate and volumetrically heat GAC particles, heavy siloxane molecules may be de-polymerized into lighter, more easily desorbed, compounds. This ability is a major advantage over thermal carbon regeneration, because heavy molecules accumulate in GAC after thermal regeneration, limiting the number of activation cycles carbon can by subject to before its performance is inadequate.

The SiC catalyst is an excellent microwave absorber and acts as an oxidizing catalyst in the microwave field. Consequently, siloxanes and $H_2S$ in the sweep gas from the microwave regeneration reactor can be oxidized at lower temperatures than in a conventional catalyst bed. The microwave-induced oxidation starts at room temperature and the SiC bed temperature increases rapidly when microwaves are applied. The efficiency of the microwave SiC bed oxidization is greater than 99% for hydrocarbons in air.

Subsequently, the $SO_2$ reacts with carbon as soon as microwave energy is applied to a GAC bed to produce carbon dioxide and elemental sulfur that can be captured by a filter. Consequently, no secondary air pollutants are produced from the microwave biogas treatment process.

The unique characteristics of microwave energy are utilized to significantly enhance chemical reactions and solvent desorption from saturated carbon. A microwave regeneration and treatment system has been constructed that can regenerate GAC at costs ranging from $0.20 to $0.60 per pound. The regeneration system can be scaled from a few pounds per hour of GAC regenerated at the biogas source to 500 pounds per hour or more for a large or regional treatment facility.

The GAC is an excellent microwave absorbent and its temperature increases rapidly when exposed to microwaves. The siloxanes adsorbed onto the GAC will be de-polymerized into smaller molecules during the microwave regeneration. Consequently, siloxanes desorb easily by microwave energy and GAC recovers its original adsorption capacity. For comparison, the rate of microwave solvent desorption is an order of magnitude greater than the conventional thermal desorption rate.

A two-stage adsorption system is used to remove siloxanes and $H_2S$ from the biogas simultaneously. The adsorber system is preceded by a water separator and equipped with the inlet and outlet valves that can easily change the flow direction. A two stage radial adsorber is preferred for higher flow rates at lower backpressure.

The biogas typically flows into a water knockout pot or a refrigerated condenser to remove free water in the biogas prior to entering into the adsorption system. The water free gas enters the adsorber containing the oldest media (first-stage or primary adsorber). Note that the GAC media adsorption capacity for siloxanes increases with decreasing moisture content in biogas. The gas leaving the first-stage adsorber flows into the adsorber containing fresh or regenerated media (second-stage or secondary adsorber). Consequently, whenever the saturated media is removed from the first-stage adsorber, the inlet and outlet valves are reversed to change the gas flow direction. As a result, the first-stage adsorber containing regenerated media becomes the second-stage adsorber.

The GAC adsorption capacity for $H_2S$ is about 5-15% by weight. If 3,000 lbs GAC adsorbers are used, GAC in the first-stage adsorber needs to be changed every 100 days for a 100 kW biogas power generating facility for 500 ppm $H_2S$. For a 400 kW biogas generator, the GAC in the first-stage adsorber needs to be changed every 25 days. This carbon change-out schedule is much shorter for digesters producing $H_2S$ concentration greater than 500-ppm.

As shown in Table 1, the molecular weight of siloxanes is much greater than the MW of $H_2S$ and vapor pressure of siloxanes is much lower than $H_2S$. The adsorption capacity of GAC for siloxane is about one tenth that of $H_2S$, but the concentration of siloxane is also a fraction of the $H_2S$ concentration. Consequently, the presence of siloxanes should not increase the GAC change-out cycle significantly.

The two-stage media adsorption system should remove 99.9% of the siloxanes and $H_2S$ from the biogas. For biogases containing $H_2S$ concentration greater than 500 ppm, an iron sponge or other commercially available $H_2S$ removal system should be installed prior to the GAC adsorber system. The $H_2S$ removal efficiency of the conventional iron sponge system is about 80%.

An embodiment of the invention is an apparatus for removing siloxane adsorbed in adsorbent media and decomposing the siloxane that comprises a first microwave reactor having a source of microwave energy, where the first microwave reactor is configured to receive adsorbent media containing siloxane, where siloxane is removed from the adsorbent media when exposed to microwave energy in the first microwave reactor, means for forming silicon dioxide from siloxane fluidly connected to the first microwave reactor, and a source of sweep gas connected to the first microwave reactor, where sweep gas flows from the sweep gas source through the first microwave reactor and through the means for forming silicon dioxide.

An aspect of the invention is where the adsorbent media contains hydrogen sulfide, where hydrogen sulfide is removed from the adsorbent media when exposed to microwave energy in the first microwave reactor, where hydrogen sulfide is transported by the sweep gas from the first microwave reactor to the means for forming silicon dioxide, and where elemental sulfur is formed from hydrogen sulfide in the means for forming silicon dioxide.

Another aspect of the invention is a biogas adsorber fluidly connected to the first microwave reactor, where the biogas adsorber is configured to contain the adsorbent media, means for transporting the adsorbent media from the biogas adsorber to the first microwave reactor, a particulate filter fluidly connected to the means for forming silicon dioxide, where biogas containing siloxane is passed through the adsorbent media in the biogas adsorber, and where the sweep gas flows from the means for forming silicon dioxide through the filter and to the biogas adsorber.

A further aspect of the invention is where the biogas contains heavy hydrocarbons having a molecular weight greater than forty five, where heavy hydrocarbons are adsorbed from the biogas in the adsorbent media, where heavy hydrocarbons are removed from the adsorbent media when exposed to microwave energy in the first microwave reactor, where heavy hydrocarbons are transported by the sweep gas from the first microwave reactor to the means for forming silicon dioxide, where methane is formed from heavy hydrocarbons in the means for forming silicon dioxide, and where methane is transported by the sweep gas from the means for forming silicon dioxide to the biogas adsorber.

A still further aspect of the invention is a second microwave reactor fluidly coupled to the first microwave reactor, a reducing agent positioned in the second microwave reactor, a source of microwave energy coupled to the second microwave reactor, and a source of water fluidly connected to the second microwave reactor, where silicon dioxide is formed when water is combined with siloxane and exposed to microwave energy in the second reactor.

Another aspect of the invention is where the reducing agent comprises carbon.

A further aspect of the invention is a second microwave reactor fluidly connected to the first microwave reactor, an oxidation catalyst positioned in the second microwave reactor, a source of microwave energy coupled to the second microwave reactor, and a source of oxygen fluidly connected to the second microwave reactor, where silicon dioxide is formed when oxygen is combined with siloxane and exposed to microwave energy in the second reactor.

A yet further aspect of the invention is a first means for filtering fluidly connected to the second microwave reactor, a third microwave reactor fluidly connected to the first means for filtering, where the third microwave reactor has a source of microwave energy, a reducing agent positioned in the third microwave reactor, and a second means for filtering, the second means for filtering fluidly connected to the third microwave reactor, where the sweep gas flows from the second microwave reactor, through the first filtering means, through the third microwave reactor and through the second filtering means.

Another aspect of the invention is where the adsorbent media contains hydrogen sulfide, where hydrogen sulfide is transported by the sweep gas from the adsorbent media in the first microwave reactor to the second microwave reactor, where hydrogen sulfide is combined with oxygen when exposed to microwave energy in the second microwave reactor to form sulfur dioxide, where sulfur dioxide is transported to the third microwave reactor by the sweep gas, where hydrogen sulfide is reduced to elemental sulfur in the third microwave reactor when exposed to microwave energy, and where elemental sulfur is removed from the sweep gas by the second filtering means.

A further aspect of the invention is where the adsorbent media comprises carbon, where the oxidation catalyst comprises silicon carbide, and where the reducing agent comprises carbon.

A still further aspect of the invention is where the reducing agent further comprises a metal oxide.

Another embodiment of the invention is an apparatus for removing siloxane, and hydrogen sulfide adsorbed in adsorbent media and decomposing the siloxane and hydrogen sulfide that comprises a first microwave reactor having a source of microwave energy, where the first microwave reactor is configured to receive adsorbent media containing siloxane and hydrogen sulfide, a second microwave reactor fluidly connected to the first microwave reactor, the second microwave reactor having a source of microwave energy, a first particulate filter fluidly connected to the second microwave reactor, where the first filter is configured to remove particulate silicon dioxide and sulfur, and a source of sweep gas connected to the first microwave reactor, where sweep gas flows from the sweep gas source through the first microwave reactor, through the second reactor and through the first filter.

Another aspect of the invention is where the adsorbent media is positioned in the first microwave reactor, where siloxane and hydrogen sulfide are removed from the adsorbent media when exposed to microwave energy, where siloxane and hydrogen sulfide are transported by the sweep gas from the first microwave reactor to the second microwave reactor, where water is introduced into the second microwave reactor, where silicon dioxide is formed in the second microwave reactor when siloxane and water are exposed to microwave energy, where silicon dioxide is removed from the sweep gas in the first filter, where sulfur is formed in the second microwave reactor when hydrogen sulfide is exposed to microwave energy, and where sulfur is removed from the sweep gas in the first filter.

A further aspect of the invention is a biogas adsorber fluidly connected to the first microwave reactor, where the adsorbent media is positioned in the biogas adsorber, where biogas containing siloxane and hydrogen sulfide is passed through the adsorbent media in the biogas adsorber, where the adsorbent media is transported to the first microwave reactor, and where the sweep gas flows from the first filter to the biogas adsorber.

A still further aspect of the invention is an oxidation catalyst positioned in the second microwave reactor, a third microwave reactor fluidly connected to the first filter, where the third microwave reactor has a source of microwave energy, a reducing agent positioned in the third microwave reactor, a second filter fluidly connected to the third microwave reactor, where the second filter is configured to remove sulfur from the sweep gas, and a source of oxygen connected to the second reactor, where the sweep gas flows from the first filter, through the third microwave reactor and through the second filter.

A further embodiment of the invention is a method for removing siloxane from adsorbent media and decomposing the siloxane that comprises providing a first microwave reactor having a source of microwave energy, where the first microwave reactor is configured to receive adsorbent media containing siloxane, providing a second microwave reactor having a source of microwave energy fluidly connected to the first microwave reactor, providing a sweep gas flowing through the first microwave reactor and the second microwave reactor, positioning adsorbent media containing siloxane in the first microwave reactor, applying microwave energy to the first microwave reactor to remove siloxane from the adsorbent media, transporting siloxane to the second reactor by the sweep gas, introducing water into the second reactor, and applying microwave energy to the second microwave reactor to form silicon dioxide from siloxane.

Another aspect of the invention is where the second microwave reactor contains a reducing agent.

A further aspect of the invention is where the adsorbent media contains hydrogen sulfide, applying microwave energy to the first microwave reactor to remove hydrogen sulfide from the adsorbent media, transporting hydrogen sulfide in the sweep gas from the first microwave reactor to the second microwave reactor, and forming elemental sulfur from hydrogen sulfide when exposed to microwave energy in the second microwave reactor.

A still further aspect of the invention is providing a first particulate filter fluidly connected to the second microwave reactor, providing an adsorber fluidly connected to the first microwave reactor, positioning the adsorbent media in the adsorber, flowing biogas containing siloxane through the adsorbent media in the adsorber, adsorbing siloxane from the biogas into the adsorbent media, transporting the adsorbent media containing siloxane to the first microwave reactor, flowing the sweep gas from second microwave reactor, through the first filter and into the adsorbent media in the adsorber, and removing silicon dioxide from the sweep gas in the first filter.

Another aspect of the invention is where the biogas contains heavy hydrocarbons having molecular weight greater than forty five, adsorbing heavy hydrocarbons from the biogas into the adsorbent media, transporting the adsorbent media to the first microwave reactor, applying microwave energy to the first microwave reactor to remove heavy hydrocarbons from the adsorbent media, transporting heavy hydrocarbons in the sweep gas from the first microwave reactor to the second microwave reactor, forming methane from heavy hydrocarbons when exposed to microwave energy in the second microwave reactor, and transporting methane from the second microwave reactor to the adsorber in the sweep gas.

A further aspect of the invention is providing an oxidizing catalyst in the second microwave reactor, providing a source of oxygen to the second microwave reactor, providing a first particulate filter fluidly connected to the second microwave reactor, providing a third microwave reactor having a source of microwave energy, where the third microwave reactor is fluidly connected to the second microwave reactor, providing a reducing agent in the third microwave reactor, providing a second particulate filter fluidly connected to the third microwave reactor, where the sweep gas flows from the second microwave reactor through the first filter, through the third microwave reactor and through the second filter, where the adsorbent media contains hydrogen sulfide, applying microwave energy to the first microwave reactor to remove hydrogen sulfide from the adsorbent media, transporting siloxane and hydrogen sulfide in the sweep gas from the first microwave reactor to the second microwave reactor, forming silicon dioxide from siloxane when exposed to microwave energy in the second microwave reactor, removing silicon dioxide in the first filter, forming sulfur from hydrogen sulfide when exposed to microwave energy in the second microwave reactor, transporting sulfur dioxide in the sweep gas from the second microwave reactor to the third microwave reactor, forming sulfur from sulfur dioxide when exposed to microwave energy in the third microwave reactor, and removing sulfur from the sweep gas in the second filter.

Another aspect of the invention is where the adsorbent media is carbon, where the oxidizing catalyst is silicon carbide, and where the reducing agent is carbon.

A further aspect of the invention is providing a metal oxide in the reducing agent.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

DETAILED DESCRIPTION OF THE INVENTION

Referring more specifically to the drawings, for illustrative purposes the present invention is embodied in the apparatus generally shown in FIG. 1 through FIG. 5. It will be appreciated that the apparatus may vary as to configuration and as to details of the parts, and that the method may vary as to the specific steps and sequence, without departing from the basic concepts as disclosed herein.

Figure 1:
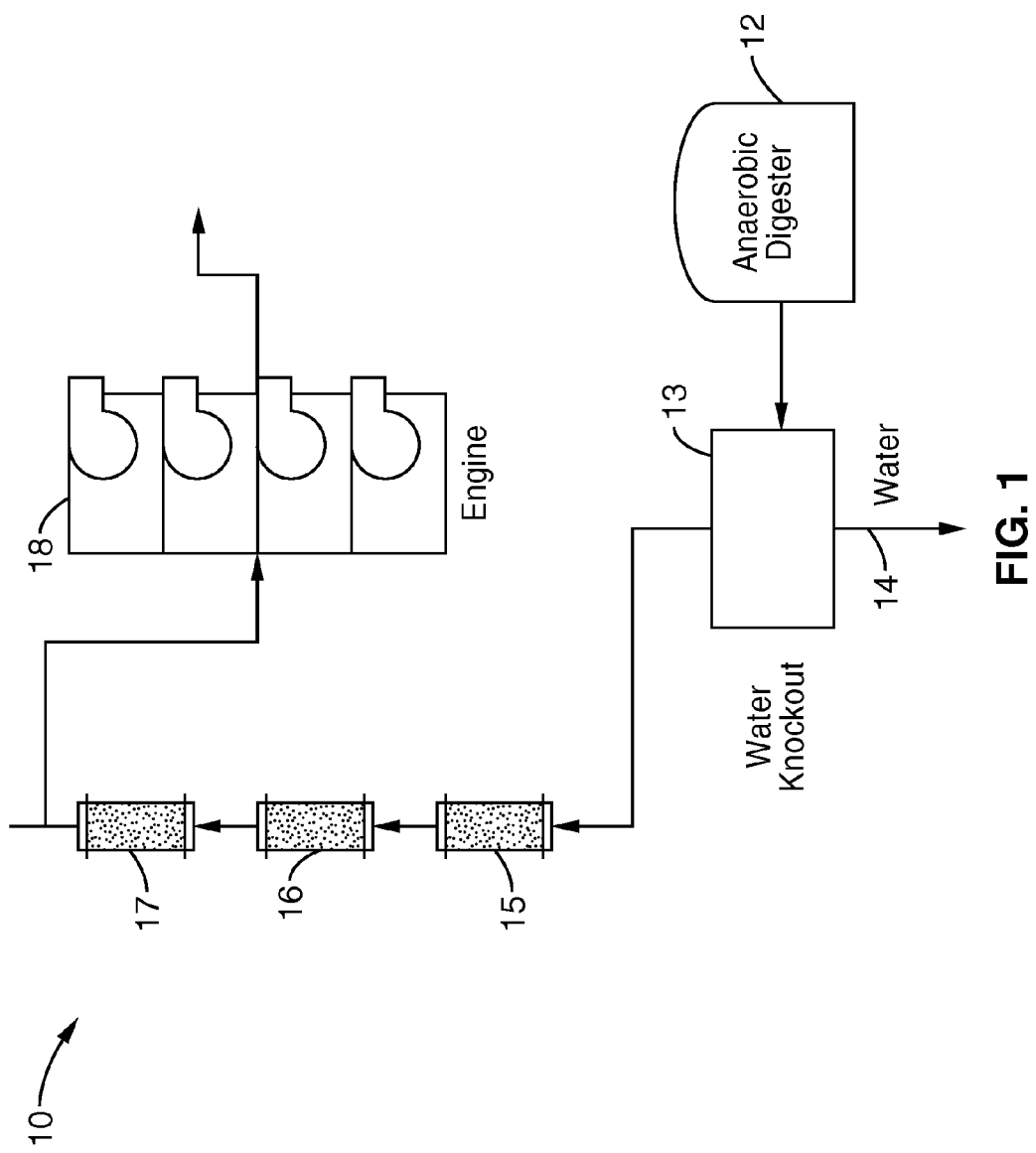
FIG. 1 is a schematic view of a process to remove siloxane and hydrogen sulfide from biogas using media adsorption.

FIG. 1 is a schematic view of a process 10 for removing siloxane and hydrogen sulfide ($H_2S$) contaminants from biogas. Biogas is primarily methane generated by bacteria in anaerobic conditions such as a digester or landfill 12. Raw biogas flows from the digester to a water knock out 13, such as a chiller system, to remove excess water 14. The biogas then flows to media adsorption vessels 15, 16, and 17 also called adsorbers.

Media adsorbers 15, 16, 17, contain an absorbent media, such as Granulated Activated Carbon (GAC), and remove $H_2S$ and siloxanes from the biogas through a chemisorption process. Some water present in the biogas is also adsorbed by the GAC. Typically, two adsorbers are in use at a time so that one can be serviced while the other is in operation. In some systems the flow of biogas can be reversed between any two vessels. Valves and controls are omitted for clarity.

The cleaned biogas flows from adsorbers 15, 16, 17, to an engine, turbine or boiler 18 to make heat, steam and/or electricity. Alternatively, the cleaned biogas is flared. In a typical operation, the media in one of the adsorbers 15, 16, 17, is removed when breakthrough of $H_2S$ or siloxanes occurs and is replaced with fresh or regenerated media. In one embodiment, adsorbers 15, 16, and 17 are portable and can be removed from the system and transported as a canister containing media.

If hydrogen sulfide levels are higher than about 500 ppm in the biogas, a sulfur removal system such as an iron sponge (not shown) may be used to reduce the high level of sulfur prior to adsorbers 15, 16, and 17.

In one embodiment of the invention, GAC in adsorbers 15, 16 and/or 17 is impregnated with a metal oxide, such as sodium hydroxide to increase adsorption capacity for $H_2S$ and siloxanes.

In another embodiment of this invention, each adsorber 15, 16, and 17 contain media selected for a specific chemical property or pore size that corresponds to a specific range of contaminant molecular weights. For example, adsorber 15 may have media with larger pores (2.5 to 3.5 nm) for siloxanes with a molecular weight over 250, and adsorber 17 may have media with smaller pores (0.7-2.5 nm) for siloxanes or contaminants with a molecular weight of 100 or less. By sequencing or layering these media in the order of largest pore structure down to the smallest, removal efficiencies of 50% greater than a homogenous bed of media can be realized before breakthrough of a siloxane species. A select media can also be specified for a particular compound found in a biogas source. The media in each adsorber can be regenerated separate from the others to maintain the media properties in each adsorber.

Media such as GAC, pelletized activated carbon (PAC), zeolites, molecular sieve and silica gel may be specified for each adsorber depending on the composition of the contaminants in the biogas and the desired pore characteristics in each adsorber.

Media which will adsorb siloxane, hydrogen sulfide and/or water and which will absorb microwave energy are preferred. Media that will regenerate the pore sites when exposed to microwave energy are most preferred.

Table 2 is an example of a material balance for a system with a flow rate of 100 SCFM with a composition of 55% methane, 44.9% $CO_2$, and 50 ppmv $H_2S$, and trace siloxanes. Here, four media adsorbers are used. The performance of four media, each with different pore sizes from larger to smaller, are estimated to complete the material balance.

The removal performance of the example media is presented in Table 3. The multi-stage adsorption system is expected to remove at least 90% of the siloxanes and $H_2S$ present in the biogas.

Figure 2:
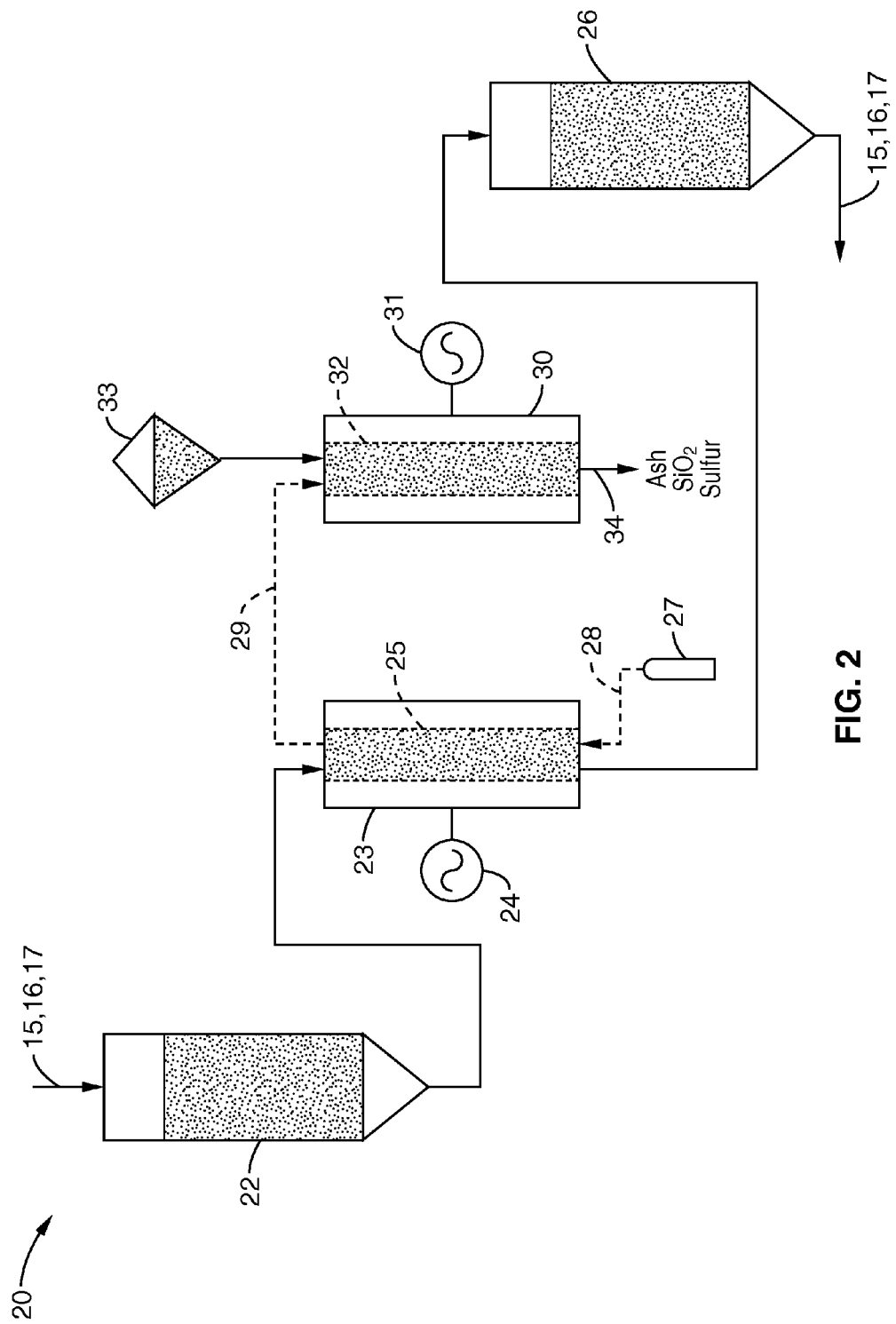
FIG. 2 is a schematic view of an apparatus for removing siloxane and $H_2S$ from media with a microwave regeneration system and forming inert components from the contaminants.

FIG. 2 illustrates a process flow diagram for a microwave regeneration system 50 for regenerating the saturated media from vessels 15, 16, and 17 shown in FIG. 1. Valves and controls have been omitted for clarity. If the microwave regeneration system is not co-located with the adsorbers 15, 16, 17, the media saturated with siloxane, $H_2S$ and water is transported to the microwave regeneration facility in bulk or in portable adsorption vessels. The contaminated media is stored in the media feed tank 22.

A first microwave reactor 23 has a source of microwave energy 24 and a vertical tube 25 that is transparent to microwave energy. In one embodiment, vertical tube 25 is made of quartz glass.

The saturated media from media hopper 22 is placed in vertical tube 25 in microwave reactor 23. The media is exposed to microwave energy in tube 25. It is preferable that tube 25 be sealed from air (oxygen) when exposed to microwave energy to prevent oxidizing the GAC. After microwave treatment, media is removed from tube 25 and transported to the regenerated media container 26 where it can be reused in adsorbers 15, 16 and 17.

A low volume, inert, sweep gas, such as Nitrogen 27, flows in tube 28 in a countercurrent direction through tube 25 in first microwave reactor 23. The siloxanes and $H_2S$, as well as water and high molecular weight hydrocarbons are desorbed rapidly from the media when exposed to microwaves. Some siloxanes may be de-polymerized at the carbon surface by microwave energy to produce lower molecular weight siloxanes before desorbing from the media. As a result of the exposure to microwave energy, no siloxane, water or hydrocarbon components will remain in the media. The power level of the microwave, the duration of media exposure, and flow rate of sweep gas are controlled to remove the siloxane components from media but not decompose the siloxanes into $SiO_2$. The active pores of the media are also regenerated by exposure to the microwave energy in this step.

The media can be regenerated in microwave reactor 23 in batch mode or continuous flow mode.

Siloxanes, water vapor and any VOCs desorbed from the media are transported out of microwave reactor 23 by the sweep gas in tube 29 to a reduction microwave reactor 30 having a source of microwave energy 31 and a vertical tube 32 that is transparent to microwave energy. Tube 32 contains a reducing agent such as GAC.

The GAC is an excellent microwave absorbent and also reducing agent for hydrocarbons. Consequently, the siloxanes will react with water in the presence of the GAC bed when exposed to microwave energy to produce methane and $SiO_2$ as shown in two examples below:

$$Si_2(CH_3)_6O \text{ (Hexamethyldisiloxane)} + 3H_2O \rightarrow 6CH_4 + 2SiO_2$$

$$Si_5(CH_3)_{10}O_5 \text{ (Decamethylcyclopentasiloxane)} + 5H_2O \rightarrow 10CH_4 + 5SiO_2.$$

Other siloxanes species and siloxane containing hydrocarbons react with water when exposed to microwave energy in the reduction reactor following a similar reaction path as shown above. If the media from adsorber 15, 16, 17 is unusually dry, water can be introduced into sweep gas in tube 29 and into reduction reactor 30.

If hydrogen sulfide is present in the biogas, it will be adsorbed in the media in adsorbers 15, 16, 17 and desorbed from the media in microwave reactor 23 in the presence of microwave energy and removed in sweep gas in tube 29. Biogas from a landfill may have 1-2% oxygen. Some media, such as GAC, will adsorb a fraction of this oxygen. If oxygen is present in the sweep gas or in the GAC, hydrogen sulfide will preferentially form water in reactor 30:

$$H_2S + \tfrac{1}{2}O_2 \rightarrow H_2O + S.$$

When all oxygen is removed or consumed, hydrogen sulfide is dissociated into hydrogen and elemental sulfur in the presence of the reducing agent when exposed to microwave energy in reduction reactor 30 as shown below:

$$H_2S \rightarrow H_2 + S.$$

Any high molecular weight VOCs containing Oxygen will decompose to form $CO_2$ and lower molecular weight hydrocarbons such as methane in reduction reactor 30. Other hydrocarbons will crack to lower molecular weight hydrocarbons, such as methane, and release hydrogen in the presence of microwave energy. The reactants then exit reactor 30 at outlet 34 for disposal. If halogenated hydrocarbons are present, the GAC in the reduction reactor 30 can be impregnated with a metal oxide such as NaOH. The sodium will react with the halogens to produce halogen salts, such as NaCl, that will be removed as a particulate at outlet 34. Ash from reacted GAC is also removed at outlet 34.

The volume of reactants at outlet 34 is very small compared to the volume of biogas treated. The reactants can be further treated by filtering the particulates or passing the remaining gasses through a flare if desired.

In one embodiment, reactor 23 and reactor 30 share the same source of microwave energy. In another embodiment, vertical tube 25 and vertical tube 32 are positioned in the same microwave reactor with the same source of microwave energy.

Figure 3:
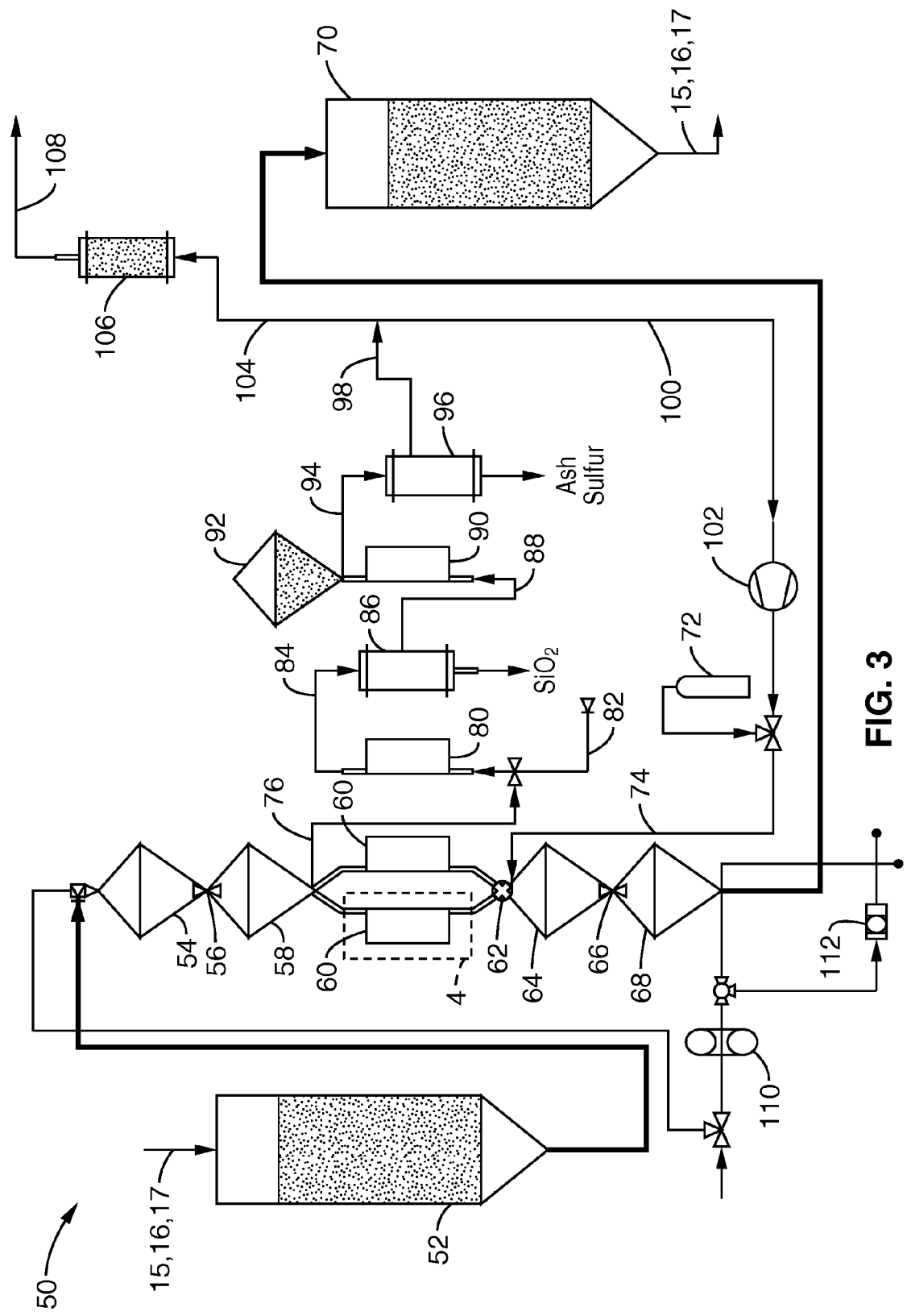
FIG. 3 is a schematic view of another embodiment for removing siloxane and hydrogen sulfide from media and filtering solids.

FIG. 3 illustrates a process flow diagram for another embodiment of a microwave regeneration system 50 for regenerating the saturated media from vessels 15, 16, and 17 shown in FIG. 1. If the microwave regeneration system is not collocated with the adsorbers 15, 16, 17, the media saturated with siloxane, $H_2S$ and water is transported to the microwave regeneration facility in bulk or in portable adsorption vessels. The contaminated media is stored in the media feed tank 52. From there, it is transported to the feed hopper 54 of the microwave regeneration system.

Figure 4:
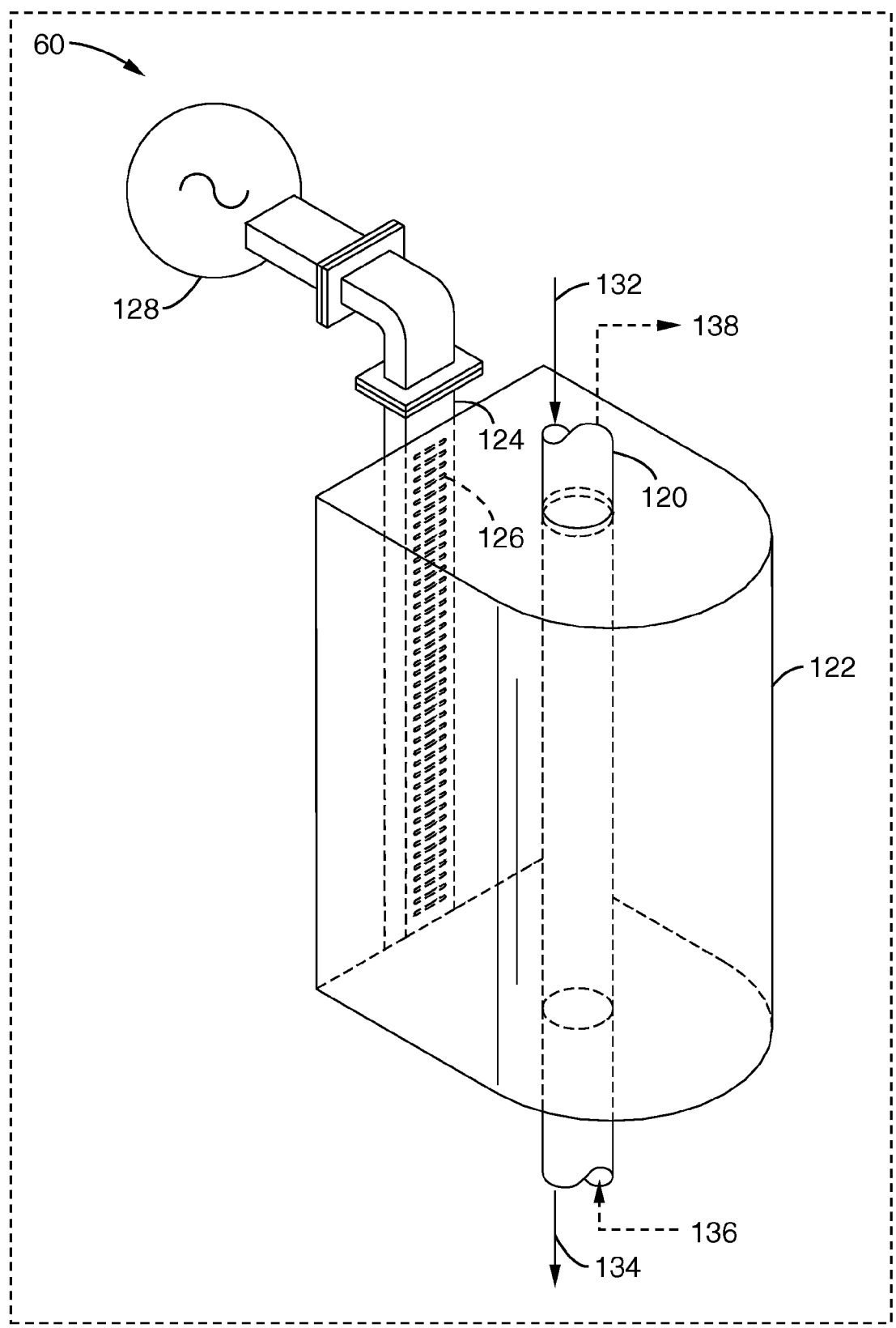
FIG. 4 is a schematic view of a microwave reactor used in the apparatus in FIG. 2 and FIG. 3.

The saturated media in the feed hopper 52 flows downward by gravity through a valve 56 to first lock hopper 58. Valve 56 prevents air (containing oxygen) from moving from feed hopper 54 to lock hopper 58. The media then flows into the first microwave reactor 60. In this illustration, two parallel reactors 60 are shown to increase media throughput and provide redundancy. Details of an embodiment of microwave reactor 60 are shown in FIG. 4.

Returning to FIG. 3, media flows from the feed hopper 58, through first microwave reactor 60, through a rotary feeder valve 62 that regulates the flow of media, and into lower lock hopper 64, through valve 66 and into discharge hopper 64. From there, the media is transported to the regenerated media container 70.

A low volume inert sweep gas, such as Nitrogen 72, flows in tube 74 into lower lock hopper 64 and in a countercurrent direction through first microwave reactor 60. Because media such as GAC is an excellent microwave absorbent, its temperature increases rapidly when exposed to a microwave field. The rate of microwave solvent desorption in the microwave field is an order of magnitude greater than the conventional thermal desorption rate. The rapid heating and strong reducing character of activated carbon in the regeneration system can also "crack" larger organic molecules that are difficult to desorb using conventional regeneration technologies. The resulting smaller molecules are then more easily removed from the carbon.

The siloxanes, $H_2S$, water and any large molecular weight hydrocarbons (VOCs), are desorbed rapidly from the media when exposed to microwave energy in first microwave reactor 60. Some siloxanes are de-polymerized at the media surface by microwave energy to produce lower molecular weight siloxanes. As a result of the microwave energy, no siloxane components will remain in the media. The desorbed gases are transported out of the first microwave reactor 60 by the low volume sweep gas and into tube 76. The power level of the microwave, the flow rate of media, and flow rate of sweep gas are controlled to remove the siloxane components from media without decomposing the siloxanes into $SiO_2$. The active pores of the media are also regenerated by exposure to the microwave energy in this step.

Next, desorbed siloxanes, water, $H_2S$ and any VOCs are transported by the sweep gas in tube 76 to a second microwave reactor 80 with a source of microwave energy and a silicon carbide (SiC) bed. A regulated source of oxygen, such as air, is introduced to the sweep gas that flows to second reactor 80 through tube 82. Siloxanes, $H_2S$ and VOCs are oxidized in the silicone carbide (SiC) bed by applying microwave energy to produce $SO_2$, water vapor, and $CO_2$ gas and particulate $SiO_2$. These gases produced in the microwave oxidizer and the sweep gas entrain the particulate $SiO_2$ and flow into tube 84 and enter into a first particulate filter 86 to remove granular $SiO_2$. In one embodiment, first filter 86 is a cleanable or vibrating filter. A cyclone may also be integrated into particulate filter 86.

The remaining gases then flow through tube 88 and into a third microwave reactor 90 having a source of microwave energy and containing a reducing agent. GAC is an excellent microwave energy absorber and also strong reducing agent. It has been demonstrated that $SO_2$ reacts with GAC in the presence of microwaves to produce elemental particulate sulfur and carbon dioxide:

$$SO_2 + C \rightarrow S + CO_2.$$

GAC is consumed in this reaction and replenished from GAC feed hopper 92.

The sweep gas and particulate sulfur flows out from the third microwave reactor 90 through tube 94 and enters into a second particulate filter 96 that captures the elemental sulfur and remaining ash from consuming GAC. In one embodiment, particulate filter 96 is a cleanable or vibrating filter. A cyclone may be integrated into second particulate filter 96. A gas cooler may also be integrated into filter 96 to increase removal efficiency. The filtered sweep gas leaves second filter 96 through tube 98 and is now clean gas consisting mostly of nitrogen, $H_2O$, and $CO_2$.

A part of the clean gas leaving the second filter is recycled back through tube 100 and a recycle compressor 102 to flow into tube 74. Any excess clean gas flows through tube 104 and through a final GAC adsorber 106 to ensure that there are no fugitive contaminants in the clean gas before venting to the atmosphere at 108.

If halogenated hydrocarbons are present, the GAC in feed hopper 92 can be impregnated with a metal oxide, such as NaOH. This will produce halogen salt particles, such as NaCl, that will be removed in second particulate filter 96. Alternatively, the clean gas in 104 can be bubbled through a wet scrubber or sparger containing a caustic solution, such as water and sodium hydroxide. The sodium in a sodium hydroxide sparger will react with the halogen in the vent gas to form a salt solution that can be safely discarded.

The regenerated media that passed through first microwave reactor 60 flows through rotary valve 62 and into lock hopper 64. From there the media flows through valve 66 and into discharge hopper 68. The media is then transported from discharge hopper 68 to the regenerated GAC storage tank 70. In one embodiment, a pneumatic blower 110 is used to transport the GAC through the system. A particulate filter 112 is used to filter out carbon fines from handling and transporting the GAC. Alternatively, a mechanical transport system is used to transport the media through microwave reactor 60.

The pores in the regenerated media are reactivated by the exposure to microwave energy in microwave reactor 60 and typically have the same or better adsorption capacity as new media. The regenerated media in storage tank 70 is transported back to the adsorption vessels 15, 16, 17 shown in FIG. 1 to further clean the biogas. Depending on attrition due to reaction or handling, new media may need to be added to regenerated media storage tank 70.

It is estimated that this process can remove siloxane and $H_2S$ from biogas, and regenerate media at a cost less than replacing contaminated media with new media.

The apparatus in FIG. 2 and FIG. 3 uses many conventional accessories like pumps, valves, gages, switches, controllers, etc. which are necessary for safe operation of the process but are outside the necessary components of the present invention and omitted for clarity.

Table 4 presents the material balance for an example regeneration system for digester gas depicted in Table 2. The material balance assumes a media regeneration rate of 100 lb/hr. The contaminant loading ratio for $H_2S$, and siloxanes was determined from the material balance for the gas pretreatment system presented in Table 3. The material balance assumes that the SiC microwave oxidizer operates with 15% excess air, and that oxidation is complete. It is also assumed that the filters for removing $SiO_2$, sulfur, and ash are 100% efficient.

An energy balance on the system indicates that 8 kW of microwave energy will be required to desorb the contaminants in the first microwave reactor 60. The SiC oxidization reactor 80 and GAC reduction reactor 90 each require about 3 kW of microwave power to heat the gas and solid substrates. There may be a requirement to cool the gas prior to entering the sulfur removal filter 96. The cooling load of 3 kW can be provided by an air cooling heat exchanger. Thus the energy required to treat 100 pounds of media is about 14 kwh or about $1.45, a fraction of other regeneration methods.

Landfill gas contains higher concentrations of heavy molecular weight hydrocarbons (molecular weight greater than 45) due to solvent disposal. Landfill gas is considered contaminated if heavy hydrocarbon loading exceeds 50 ppmv. If the example is applied to landfill gas, the media will remove all heavy hydrocarbons from the gas. The presence of the heavy hydrocarbons requires 20% to 30% more media to clean a volume of landfill gas as compared to a similar volume of digester gas. The presence of heavy hydrocarbons in the landfill gas is expected to require about 20% to 30% more electrical energy to regenerate the additional media and destroy the additional contaminants.

The example multi stage media adsorption system is expected to remove at least 90% of the siloxanes and $H_2S$ from the biogas. The microwave treatment system is expected to remove over 95% of the siloxanes and $H_2S$ from the media. There is expected to be a small (1-3%) attrition of media from handling and regeneration that will be replaced with new media.

FIG. 4 is a schematic view of a microwave reactor 60 shown in FIG. 3. A tube 120, which is transparent to microwave energy, is positioned in microwave cavity 122. Microwave cavity 122 will contain microwave energy and, in this example, is shaped similar to a rural mailbox. In one embodiment, tube 120 is quartz glass and about 4 inches in diameter to provide good microwave penetration to media in the center of the tube.

A rectangular wave guide 124 is attached to microwave cavity 122 and communicated energy through a row of slots 126. The width of the slot and spacing is optimized for microwave energy. A source of microwave energy 128 is attached to waveguide 124.

Contaminated media enters tube 120 at media inlet 132 and flow downward through the microwave field and exits at media outlet 134. Sweep gas enters at the bottom of the reactor at gas inlet 136 and flows upward through tube 120 and out at gas outlet 138. When exposed to microwave energy, gaseous contaminants are quickly desorbed from the media in tube 120 and removed in the sweep gas.

In another embodiment of the invention, microwave cavity 122 is water-cooled. In a further embodiment, microwave cavity 122 is air-cooled.

Third microwave reactor 90, shown in FIG. 3, is of similar design. Second microwave reactor 80 is of similar design except the oxidation catalyst, such as Silicon Carbide, in tube 120 is fixed.

Figure 5:
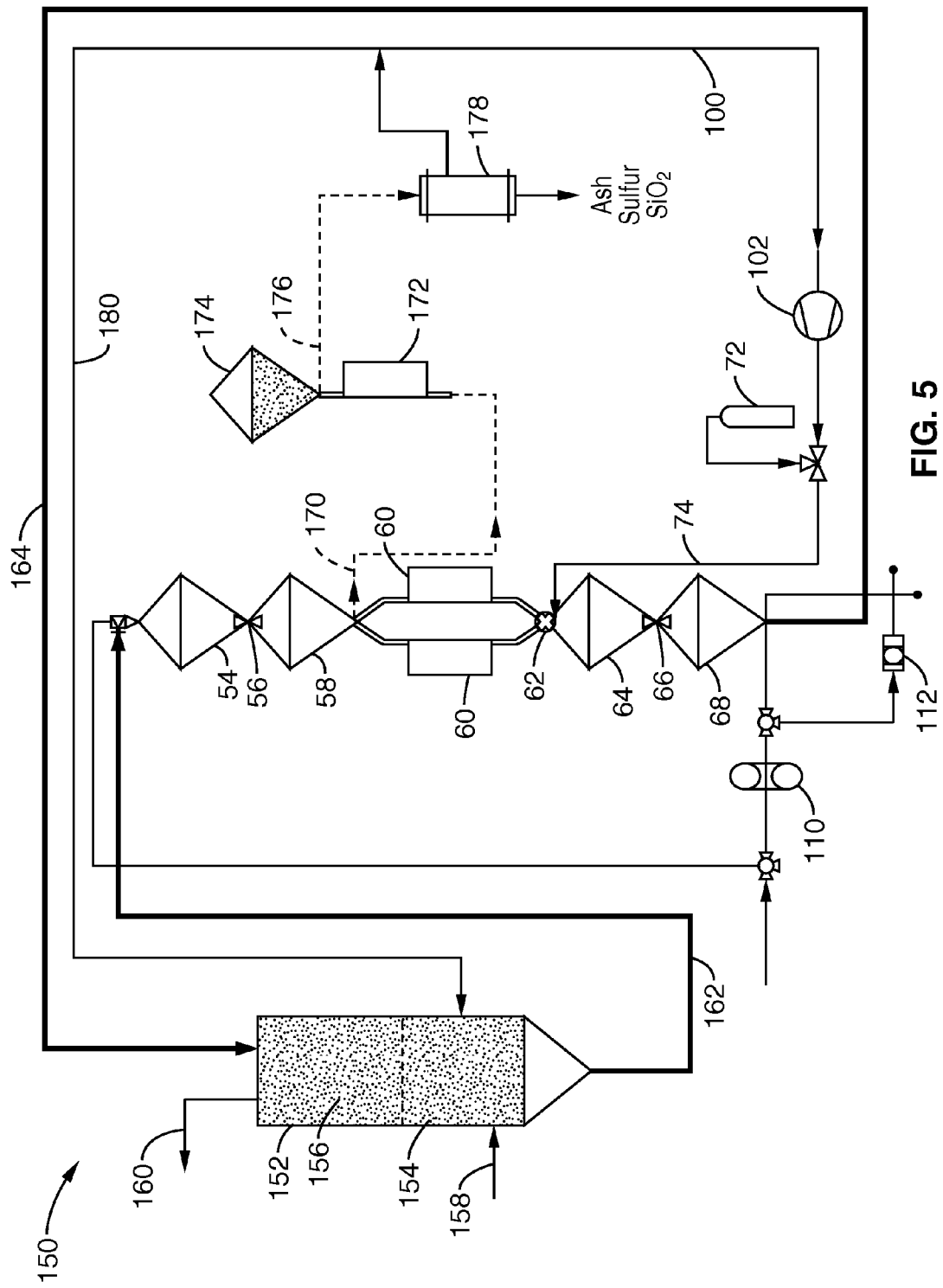
FIG. 5 is a schematic view of a system to remove siloxane and hydrogen sulfide from biogas without atmospheric emissions.

FIG. 5 is a schematic view of another embodiment of a siloxane and hydrogen sulfide removal process 150 with a media adsorber integrated into the system. In this process, some of the BTU content in contaminants such as $H_2S$, Siloxane and hydrocarbons is recovered and recycled into the biogas stream and there are no direct atmospheric emissions. Biogas produced in landfills may have up to about 5-10% hydrocarbons having a molecular weight above 45 that are derived primarily from solvents disposed in the landfill. Many of these heavy hydrocarbons contain halogens. Burning these heavy hydrocarbons in an engine, turbine or flare can cause harmful deposits or undesirable air pollution. Media such as GAC readily adsorb these heavy hydrocarbons from biogas.

Schematically, media adsorber 152 is a two-stage adsorber with primary stage 154 and secondary stage 156. When the media in primary stage 154, such as GAC, has been saturated with siloxane and $H_2S$, or breakthrough of a contaminant is detected or calculated, it is transported to feed hopper 54. Media in secondary stage 156 moves down by gravity and replaces the media removed from primary stage 154. Biogas from a digester or landfill enters media adsorber 152 at inlet 158 in primary stage 154, flows through secondary stage 156, and exits GAC adsorber 152 at outlet 160. In one mode of this embodiment, media adsorber 152 is a two stage radial adsorber with homogeneous media. In another embodiment, media adsorber 152 is a plurality of media adsorbers connected in series. The capacity of a typical commercial media adsorber ranges from about 100 pounds to about 3,000 pounds of media such as GAC.

Biogas at inlet 158 entering media adsorber 152 has been pretreated for excess water and high levels of $H_2S$ as previously described in FIG. 1. Note, however, that treated biogas typically still contains water vapor. The temperature of the biogas or the adsorber may also be slightly warmed to prevent water condensation in the media adsorber.

The contaminated media from primary stage 154 is transported through conduit 162 to the feed hopper 54 of the microwave regeneration system.

The contaminated media in feed hopper 54 flows downward by gravity through a valve 56 to first lock hopper 58 which seals air from moving from feed hopper 54 to first lock hopper 58. The media then flows into the first microwave reactor 60. In this illustration, two parallel reactors 60 are shown to increase media throughput. Media flows from the lock hopper 58, through the tube in the microwave reactor 60, and through a rotary feeder valve 62 that regulates the flow of media into lock hopper 64. The media then travels through valve 66 and into discharge hopper 64. From there, the media is transported through conduit 164 back to the secondary stage 156 of media adsorber 152. If a mechanical media transport system that does not introduce air into the system is used, feed hopper 54, lock hopper 58, lock hopper 64 and discharge hopper 68 may be eliminated from the system. Valves 56 and 66 would be used to keep biogas out of microwave reactor 60.

In a further embodiment, two or more adsorbers 152 containing different pore size media are used in series in the biogas stream. One microwave reactor 60 is dedicated to each adsorber to keep the different media separate through the regeneration process.

A low volume inert sweep gas, such as Nitrogen 72, flows in tube 74 into lower lock hopper 64 and in a countercurrent direction through first microwave reactor 60. The siloxanes and $H_2S$, as well as water and high molecular weight hydrocarbons are desorbed rapidly from the media when exposed to microwaves in first microwave reactor 60. Some siloxanes may be de-polymerized at the carbon surface by microwave energy to produce lower molecular weight siloxanes before desorbing from the media. As a result of the exposure to microwave energy, no siloxane or hydrocarbon components will remain in the media. The power level of the microwave, the flow rate of media, and flow rate of sweep gas are controlled to remove the siloxane components from media but not decompose the siloxanes into $SiO_2$. The active pores of the media are also regenerated by exposure to the microwave energy in this step.

Siloxanes, $H_2S$, water vapor and any VOCs desorbed from the media are transported out of microwave reactor 60 by the sweep gas in tube 170 to a reduction microwave reactor 172 containing a reducing agent such as GAC.

The GAC is an excellent microwave absorbent and also reducing agent for hydrocarbons. Consequently, the siloxanes will react with water vapor in the presence of the GAC bed when exposed to microwave energy to produce methane and $SiO_2$ as shown in two examples below:

$$Si_2(CH_3)_6O \text{ (Hexamethyldisiloxane)} + 3H_2O \rightarrow 6CH_4 + 2SiO_2$$

$$Si_5(CH_3)_{10}O_5 \text{ (Decamethylcyclopentasiloxane)} + 5H_2O \rightarrow 10CH_4 + 5SiO_2.$$

Other siloxanes species and siloxane containing hydrocarbons react with water vapor when exposed to microwave energy in the reduction reactor following a similar reaction path as shown above. If the media from adsorber 152 is unusually dry, water can be introduced into sweep gas in 170 and into reduction reactor 172.

Any high molecular weight VOCs containing Oxygen will decompose to form $CO_2$ and lower molecular weight hydrocarbons such as methane in reduction reactor 172. Other hydrocarbons will crack to lower molecular weight hydrocarbons, such as methane, and release hydrogen in the presence of microwave energy. The reactants then flow through tube 176 to particulate filter 178. The silicon oxide ($SiO_2$), in the form of a particulate, is removed, and the remaining gasses ($CH_4$, $H_2O$, $CO_2$, etc.) exit filter 178 and flow through tube 180 and into primary stage 154 of media adsorber 152. Methane and $CO_2$ are not readily adsorbed by the media in media adsorber 152 and exit with the biogas at outlet 160. Any remaining hydrocarbons with molecular weight higher than about 45 will become adsorbed in media in adsorber 152 and reintroduced with the media into microwave reactor 60.

If halogenated hydrocarbons are present, the GAC in the reduction reactor 172 can be impregnated with a metal oxide such as NaOH. The sodium will react with the halogens to produce halogen salts, such as NaCl, that will be removed as a particulate in filter 178. Ash from reacted GAC is also removed by filter 178. In one embodiment, particulate filter 178 is a cleanable or vibrating filter. A cyclone may be integrated with filter 178. A gas cooler may also be integrated into filter 178 to increase efficiency.

If high molecular weight siloxanes are only partially decomposed and remain in a gaseous state, they will pass through filter 178 and through tube 180 to media adsorber 152. Here they will be adsorbed again in the media and reintroduced into microwave reactor 60. Eventually, they will be decomposed to low molecular weight hydrocarbons, such as methane, and $SiO_2$. The $SiO_2$ particulates will be filtered from the system in filter 178 and the methane will pass through the media in media adsorber 152 and exit outlet 158 with the biogas.

If hydrogen sulfide is present in the biogas, it will be adsorbed in the media in adsorber 152 and desorbed from the media in microwave reactor 60 in the presence of microwave energy and removed in sweep gas 170. Biogas from a landfill may have 1-2% oxygen. Some media, such as GAC, will adsorb a fraction of this oxygen. If oxygen is present in the sweep gas or in the GAC, hydrogen sulfide will preferentially form water in reactor 172:

$$H_2S + \tfrac{1}{2}O_2 \rightarrow H_2O + S.$$

When all oxygen is removed or consumed, hydrogen sulfide is dissociated into hydrogen and elemental sulfur in the presence of the reducing agent when exposed to microwave energy in reduction reactor 172 as shown below:

$$H_2S \rightarrow H_2 + S.$$

The reactants flow through tube 176 and elemental sulfur in particulate form is removed by filter 178. Hydrogen gas flows through tube 180 to combine with biogas in media adsorber 152 and will pass through the media to outlet 160. In one mode, some of the reacted gasses from reduction reactor 172 flow through tube 100 to compressor 102 and are recycled through the microwave reactor through tube 74. Note that all excess gas from microwave reduction reactor 172 is reintroduced into the media adsorber 152 with the biogas. There are no atmospheric emissions from this system. In one mode of this process, the reacted gasses are chilled and excess water is condensed and removed from the gas in tube 180 before returning to media adsorber 152.

In one embodiment of the invention, the media in media adsorber 152 is GAC. In another embodiment of the invention, the media in media adsorber 152 is a molecular sieve.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

Common Volatile Siloxanes

| Name | Formula | MW | Vapor Press. mmHg at 77° F. | Abb. | Boiling Point,° F. | Water Solub. (mg/L), 77° F. |
|---|---|---|---|---|---|---|
| Hexamethylcyclotrisiloxane | $C_6H_{18}O_3Si_3$ | 222 | 10 | $D_3$ | 275 | 1.56 |
| Octamethylcyclotetrasiloxane | $C_8H_{24}O_4Si_4$ | 297 | 1.3 | $D_4$ | 348 | 0.056 |
| Decamethylcyclopentasiloxane | $C_{10}H_{30}O_5Si_4$ | 371 | 0.4 | $D_5$ | 412 | 0.17 |
| Dodecamethylcyclohexasiloxane | $C_{12}H_{36}O_6Si_6$ | 445 | 0.02 | $D_6$ | 473 | 0.005 |
| Hexamethyldisiloxane | $C_6H_{18}Si_2O$ | 162 | 31 | $L_2$, MM | 224 | 0.93 |
| Octamethyltrisiloxane | $C_8H_{24}Si_3O_2$ | 236 | 3.9 | $L_2$, MDM | | 0.035 |
| Decamethyltetrasiloxane | $C_{10}H_{30}Si_4O_3$ | 310 | 0.55 | $L_3$, $MD_2M$ | | |
| Dodecamethylpentasiloxane | $C_{12}H_{36}Si_5O_4$ | 384 | 0.07 | $L_4$, $MD_2M$ | | |

TABLE 2

Example Material Balance for biogas pretreatment system.

| Stream | Pressure (psig) | Temp (F.) | $CH_4$ (gmol/hr) | $CO_2$ (gmol/hr) | $H_2O$ (gmol/hr) | $H_2S$ (gmol/hr) | $C_8H_{24}O_4Si_4$ (gmol/hr) | $C_{10}H_{30}O_5Si_5$ (gmol/hr) |
|---|---|---|---|---|---|---|---|---|
| Biogas Feed Stream | 7 | 45 | 4046 | 3237 | 47 | 0.4 | 2.13E−03 | 2.42E−02 |
| Exit Media #1 | 6.5 | 55 | 4046 | 3237 | 23 | 0.06 | 2.13E−03 | 2.42E−02 |
| Exit Media #2 | 6 | 55 | 4046 | 3237 | 23 | 5.52E−02 | 1.91E−03 | 1.21E−02 |
| Exit Media #3 | 5.5 | 55 | 4046 | 3237 | 23 | 5.52E−02 | 9.56E−05 | 1.21E−03 |
| Exit Media #4 | 5 | 55 | 4046 | 3237 | 23 | 5.52E−04 | 9.56E−06 | 1.21E−04 |

TABLE 3

Example Media Performance

| | Media #1 | Media #2 | Media #3 | Media #4 |
|---|---|---|---|---|
| Media | Molecular Sieve | AFT "DD" | AFT "DM" | AFT "MD" |
| H2S removal Efficiency | 85% | 0% | 0% | 90% |
| H2O removal Efficiency | 50% | 0% | 0% | 0% |
| D4 removal Efficiency | 0% | 10% | 95% | 90% |
| D5 removal Efficiency | 0% | 50% | 90% | 90% |
| Estimated Overall Adsorption Capacity lbs adsorbent/hr | 25% 3.78 | 5% 0.200 | 5% 0.202 | 5% 0.1007 |

TABLE 4

Material Balance for Example Carbon Regeneration System

|  | Temp (F.) | Pres (psig) | GAC (lb/hr) | $H_2S$ (lb/hr) | $N_2$ (lb/hr) | $O_2$ (lb/hr) | $SO_2$ (lb/hr) | S (lb/hr) | $CO_2$ (lb/hr) |
|---|---|---|---|---|---|---|---|---|---|
| Carbon Inlet | 70.0 | 0 | 100 | 0.642 | 0 | 0 | 0 | 0 | 0 |
| Regenerated Carbon | 250 | 0.500 | 99.0 | 0 | 0 | 0 | 0 | 0 | 0 |
| Recycled Sweep Gas | 95 | 10.0 | 0 | 0 | 9.36 | 0 | 0 | 0 | 0.843 |
| Saturated Sweep Gas | 250 | 7.00 | 0 | 0.642 | 9.36 | 0 | 0 | 0 | 0.843 |
| Oxidation Air | 70.0 | 7.00 | 0 | 0 | 8.96 | 2.38 | 0 | 0 | 0 |
| Oxidized Sweep Gas | 500 | 6.00 | 0 | 0 | 18.3 | 0.522 | 1.21 | 0 | 1.43 |
| SiO2 Filter | 500 | 4.00 | 0 | 0 | 0 | 0 | 0 | 0 | 0 |
| Reacted Sweep Gas | 500 | 3.00 | 0 | 0 | 18.3 | 0 | 0 | 0.604 | 2.97 |
| Ash-Free Sweep Gas | 150 | 2.00 | 0 | 0 | 18.3 | 0 | 0 | 0 | 2.97 |
| Ash Outlet | 150 | 0 | 0 | 0 | 0 | 0 | 0 | 0 | 0 |
| Reactor Makeup Carbon | 70.0 | 0 | 0.640 | 0 | 0 | 0 | 0 | 0 | 0 |
| Sweep Gas Purge | 125 | 2.00 | 0 | 0 | 8.96 | 0 | 0 | 0 | 2.13 |
| Vent to Atmosphere | 125 | 0 | 0 | 0 | 8.96 | 0 | 0 | 0 | 2.13 |
| Nitrogen Supply | 32.0 | 15.0 | 0 | 0 | 0 | 0 | 0 | 0 | 0 |

|  | $H_2O$ (lb/hr) | Ash (lb/hr) | $C_8H_{24}O_4Si_4$ (lb/hr) | $C_{10}H_{30}O_5Si_5$ (lb/hr) | $SiO_2$ (lb/hr) |
|---|---|---|---|---|---|
| Carbon Inlet | 21.5 | 0 | 3.23E−02 | 4.59E−01 | 0 |
| Regenerated Carbon | 0 | 0 | 0 | 0 | 0 |
| Recycled Sweep Gas | 1.87 | 0 | 0 | 0 | 0 |
| Saturated Sweep Gas | 23.4 | 0 | 3.23E−02 | 4.59E−01 | 0 |
| Oxidation Air | 0 | 0 | 0 | 0 | 0 |
| Oxidized Sweep Gas | 24.1 | 0 | 0 | 0 | 0.397 |
| SiO2 Filter | 0 | 0 | 0 | 0 | 0.397 |
| Reacted Sweep Gas | 24.1 | 0.0676 | 0 | 0 | 0 |
| Ash-Free Sweep Gas | 4.6 | 0 | 0 | 0 | 0 |
| Ash Outlet | 20 | 0.0676 | 0 | 0 | 0 |
| Reactor Makeup Carbon | 0 | 0 | 0 | 0 | 0 |
| Sweep Gas Purge | 1.8 | 0 | 0 | 0 | 0 |
| Vent to Atmosphere | 1.8 | 0 | 0 | 0 | 0 |
| Nitrogen Supply | 0 | 0 | 0 | 0 | 0 |

What is claimed is:

1. A microwave reactor apparatus, comprising:
a microwave cavity configured to contain microwaves;
a rectangular waveguide attached to said microwave cavity;
a source of microwave energy attached to said rectangular waveguide;
said rectangular waveguide having a row of slots;
wherein microwave energy communicates to said microwave cavity through said row of slots; and
a tube positioned in said microwave cavity;
wherein said tube is transparent to microwave energy;
wherein said tube has an inlet and an outlet; and
wherein said tube is configured for receiving media in said inlet.

2. An apparatus as recited in claim 1, wherein said rectangular wave guide is oriented parallel to said tube.

3. An apparatus as recited in claim 1, wherein said tube comprises quartz glass.

4. An apparatus as recited in claim 1, wherein said microwave cavity is air-cooled.

5. An apparatus as recited in claim 1, further comprising:
a sweep gas inlet positioned at said tube outlet; and
a source of sweep gas connected to said sweep gas inlet.

6. An apparatus as recited in claim 1:
wherein said microwave cavity comprises a planar surface and an arc-shaped surface; and
wherein said rectangular waveguide is attached to said planar surface.

7. An apparatus as recited in claim 1, wherein said arc-shaped surface is oriented parallel to said tube.

8. An apparatus as recited in claim 1, wherein said rectangular waveguide is attached outside said microwave cavity.

9. An apparatus as recited in claim 1, further comprising:
a first rotary feeder valve connected to said tube inlet; and
a second rotary feeder valve connected to said tube outlet.

* * * * *